United States Patent
Kabat

Patent Number: 5,507,718
Date of Patent: Apr. 16, 1996

[54] METHOD AND APPARATUS FOR APPLYING NECK TRACTION

[76] Inventor: Herman Kabat, 20 Wilbur Hazard Rd., Saunderstown, R.I. 02874

[21] Appl. No.: 337,934

[22] Filed: Nov. 10, 1994

[51] Int. Cl.⁶ ........................................ A61F 5/00
[52] U.S. Cl. ...................... 602/18; 604/17; 128/DIG. 23
[58] Field of Search ................... 602/17, 18, 19; 128/DIG. 23

[56] References Cited

U.S. PATENT DOCUMENTS

| | | |
|---|---|---|
| 2,088,207 | 7/1937 | Kaiser . |
| 2,284,058 | 8/1940 | Kaiser et al. . |
| 3,220,406 | 11/1965 | Connelly .................... 602/18 |
| 4,643,174 | 2/1987 | Horiuchi . |
| 4,700,697 | 10/1987 | Mundell et al. . |
| 4,708,129 | 11/1987 | Pujals, Jr. .................... 602/18 |
| 4,782,824 | 11/1988 | Davies . |
| 4,940,043 | 7/1990 | Burns et al. . |
| 4,955,368 | 9/1990 | Heimann . |
| 4,969,453 | 11/1990 | Heimann . |
| 5,141,489 | 8/1992 | Sereboff .................... 602/18 |
| 5,211,623 | 5/1993 | Sarkozi .................... 602/18 |
| 5,289,829 | 3/1994 | Roehrig . |
| 5,320,596 | 6/1994 | Catipovic et al. .......... 602/18 |
| 5,338,289 | 8/1994 | Cooker .................... 602/19 |

Primary Examiner—Richard J. Apley
Assistant Examiner—Kim M. Lee
Attorney, Agent, or Firm—Fish & Richardson

[57] ABSTRACT

An apparatus and method to apply traction to the cervical spine to help repair, non-invasively, a herniated cervical disc. A doughnut shaped member, appropriately cushioned, is constructed using elastic springy materials. Cushioned portions are placed against the underside of the chin and against the chest, and the member is bent to a saddle shape by securing opposing sides of the member behind the neck using flexible string or strap-like connecting members. The resulting structure applies pressure to the underside of the chin, in a comfortable manner, thereby providing traction to the herniated disc.

12 Claims, 2 Drawing Sheets

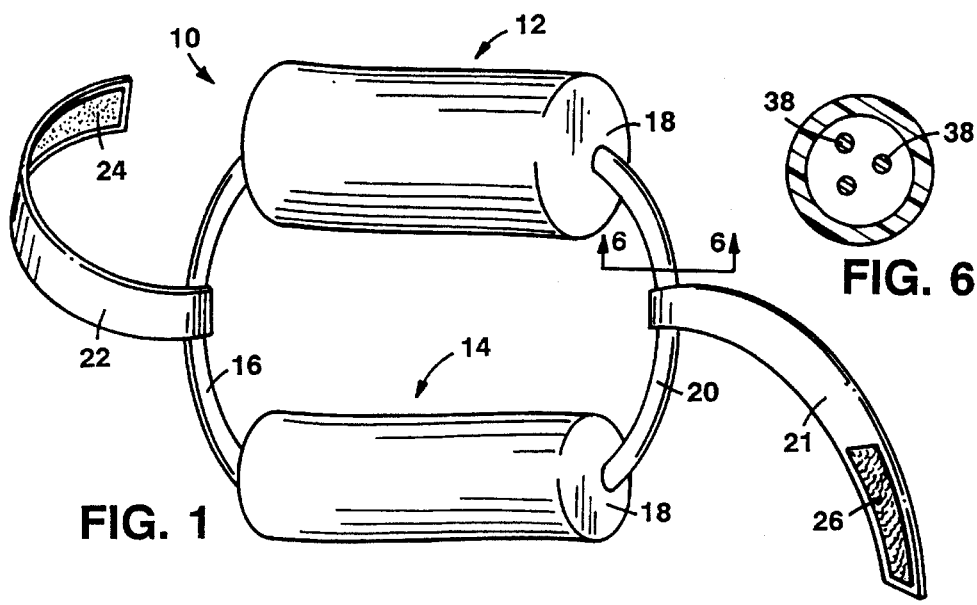
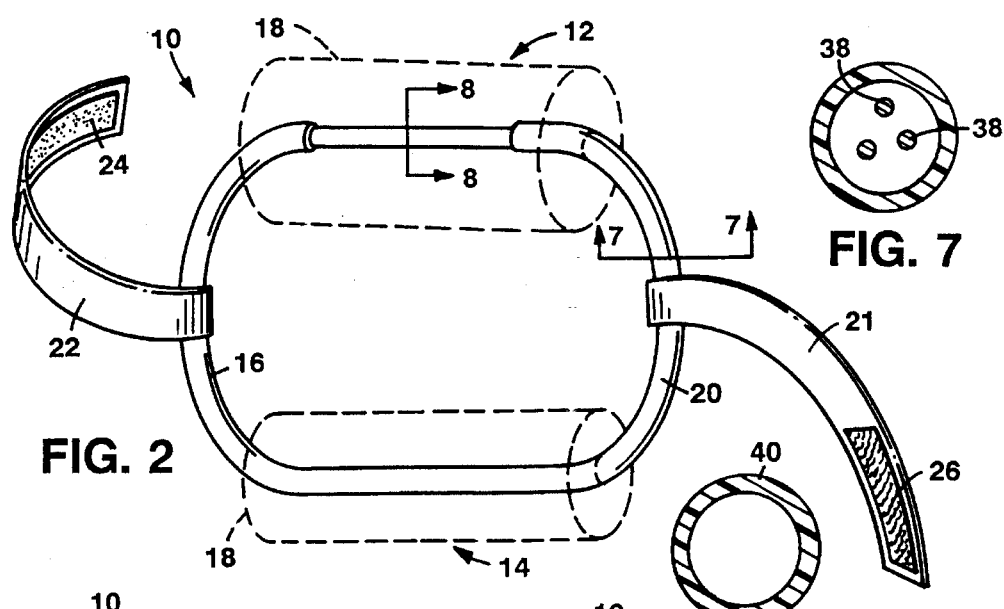
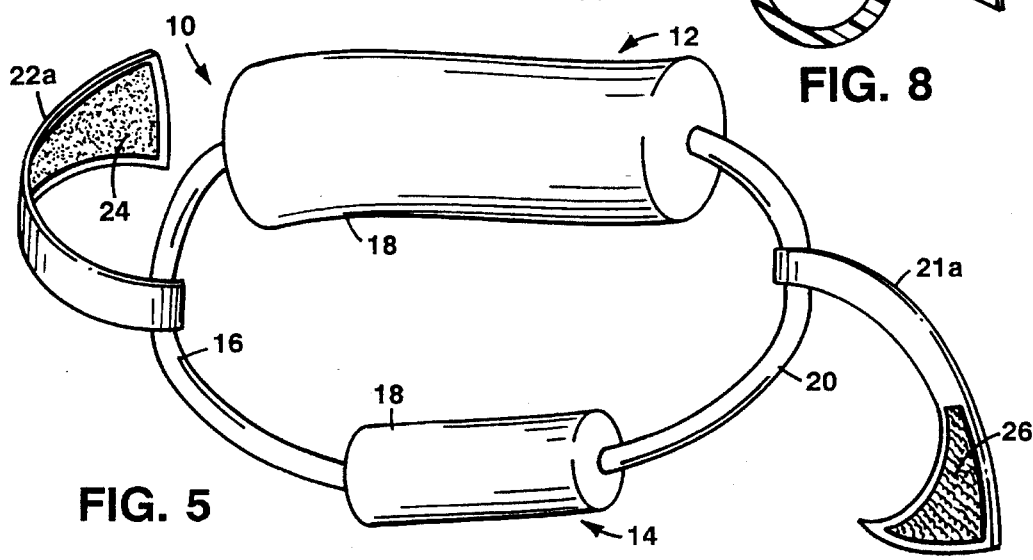

METHOD AND APPARATUS FOR APPLYING NECK TRACTION

BACKGROUND OF THE INVENTION

The invention relates generally to a method and apparatus for applying traction, and, more particularly, to a method and apparatus for effecting neck traction by applying pressure to the underside of the chin.

It is well known that the application of traction to the neck can help relocate or repair an otherwise slipped cervical disc and thereby can relieve pain in the neck, shoulder blade and arm, pain in the lower back and leg, and can also provide relief for headaches or dizziness caused by the slipped disc. Typically, however, apparatus for applying traction has been cumbersome, physically restrictive, and used as a rule only for a short period of time several times a week, either at the doctor's or therapist's office or at home.

It has been found that the application of pressure beneath the chin applies traction to the neck which has a significant healing effect. Typically, pressure might be applied beneath the chin simply by placing the palm of the hand beneath the chin and applying pressure using the arm or other hand. Unfortunately, such a treatment cannot be effectively given for a continuous twenty-four hour period, or even during the waking hours, on a continuous basis. As a result, the treatment is less effective than it might otherwise be.

It is therefore a primary object of the invention to apply continuous yet not uncomfortable pressure beneath the chin to effect traction of the cervical spine. This invention can apply neck traction continuously in any position: standing, walking, sitting, bending down, kneeling, eating, drinking, or lying in bed including during sleep. Cervical traction can also be applied at any location: outdoors, indoors, at work, while driving a car, at home or elsewhere. Other objects of the invention are a simple construction, an apparatus which does not unduly restrict the movement of the head while applying continuous pressure beneath the chin, and an apparatus which is reliable, low in cost, and comfortable.

SUMMARY OF THE INVENTION

The invention relates to an apparatus and method for applying traction to the neck, in particular to a herniated cervical disc. The invention features a substantially closed loop made of a rolling elastic, solid or hollow substantially doughnut shaped structure having first and second opposed portions connected by tension providing connecting members. The first and second opposed portions have centrally positioned cushioned surfaces. At least one, and preferably both, of the opposed portions are also flexible for enabling, at at least the one portion, a translational movement in response to lateral side to side movement of the head. First and second tension providing connecting members, which can be integral with the opposed portions, connect at each of their ends to the ends of the opposed portions to form the generally rounded structure. This construction enables the structure to be placed between a person's chin and chest to provide an upward pressure against the chin when the apparatus is held in place by tie-down members, connected at central locations along the connecting members, and secured (to each other) behind the neck. The rounded opposed portions of the structure provide at one portion, a translational movement when the head moves laterally from side to side. The opposing portions are also appropriately cushioned to provide additional comfort. The apparatus also allows movement of the head down or up or laterally. While applying traction to the cervical spine, there is no interference with swallowing or chewing and no discomfort related to pressure on the throat.

In particular embodiments of the invention, the structure is fully closed and has an elongated hollow tubing with spring material inserted in the elongated hollow interior of the tubing. The spring material provides a resilient spring action as the structure is bent or folded by the pulling action of the tie-down members. By varying the spring materials, different forces can be applied under the chin.

The spring material can be any spring-like material, for example, piano wire, coiled springs, fiberglass, teflon, or other elastic, hollow, honeycomb, or solid metal, plastic or rubber materials, etc. In a particularly preferred embodiment, the tensioning material extends around the circumference of the structure up to but not including that section of one of the opposed portions which will be positioned beneath the chin. In this manner, the surface beneath the chin can be better adapted to spread the force across the underside of the chin to improve the comfort of the device during use.

In yet another aspect of the invention, the tie-down elements can use Velcro fasteners for connecting the ends to each other.

BRIEF DESCRIPTION OF THE DRAWINGS

Other objects, features, and advantages of the invention will be apparent from the drawings, in combination with the following description, in which:

FIG. 1 is a diagrammatic representation of a first embodiment according to the invention;

FIG. 2 shows a second embodiment of the invention in which the tensioning material does not extend completely around the structure;

FIG. 5 is a diagrammatic representation of a third embodiment according to the invention;

FIG. 6 is a cross-sectional view along lines 6—6 of FIG. 1;

FIG. 7 is a cross-sectional view along lines 7—7 of FIG. 2; and

FIG. 8 is a cross-sectional view along lines 8—8 of FIG. 2.

DESCRIPTION OF PARTICULAR PREFERRED EMBODIMENTS

Figure 3:
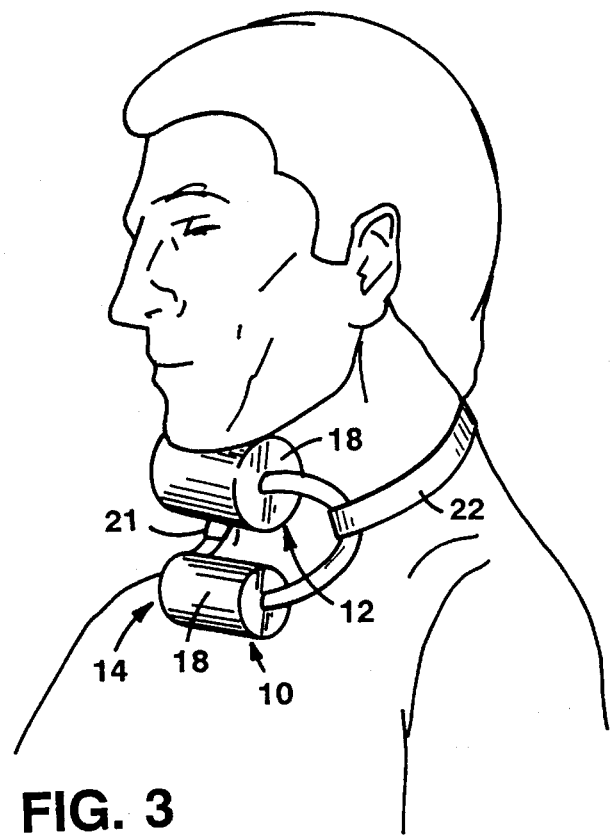
FIG. 3 is a diagrammatic representation of a side view of a person, showing the invention in use.

Research has demonstrated that, in addition to the classical symptoms of pain in the neck, shoulder blade and arm, lower back pain and leg pain, and even headaches and dizziness in some instances, can be caused by a slipped cervical disc. Such a herniated cervical disc can be corrected by various non-invasive treatments as described in the inventor's books "Low Back and Leg Pain From Herniated Cervical Disc" and "Low Back and Leg Pain From Slipped Disc in the Neck", published by Warren H. Green, Inc. in 1980 and 1983, respectively. Part of the treatment for this condition includes the application of self-applied neck traction. The present invention provides a method and apparatus for effecting neck traction, which is convenient to use and not overly uncomfortable, and which can be applied continuously for long periods of time.

Referring to FIG. 1, a traction device 10, in accordance with the invention, has opposed cushioned portions 12 and 14 connected by elongated, deformable, elastic members 16 and 20. In one embodiment of the invention, portions 12, 14 and members 16, 20 are integral and form a continuous elongated hollow tube member, the ends of which are sealingly connected in a doughnut-shaped arrangement. Prior to sealing, the interior of the tube member is filled with piano wires to provide a required spring pressure, as described below. In this particular embodiment, cushioning material 18 is provided over oppositely positioned tubular sections to provide substantial comfort during use as will be seen hereinafter.

Connecting elements 21, 22, for example fabric materials which have loop and hook connectors 24 and 26 at their ends, are secured, in any desirable way such as, for example, adhesive bonding, at central locations of members 16 and 20 of the structure.

Referring to FIG. 3, in operation, the cushioned elements 12 and 14 are positioned at the underside of the chin and on the upper chest; and while in that position, the connecting elements 21 and 22 are tensioned and fastened behind the neck. This pulls upon the structure so that it bends or folds thereby applying spring pressure to the underside of the chin and to the chest. The force against the chin is preferably at least five pounds and can advantageously be increased so long as the wearer is not unduly discomforted. The structure thus takes the shape of a saddle-like device. If needed, additional cushioning material can be provided at the back of the neck in order to increase the comfort of the device. As a result, the structure, in this illustrated embodiment, achieves the saddle shape so that upward pressure on the chin applies traction to the herniated cervical disc. Referring to FIG. 5, the connecting ends of elements 21 and 22 can, if desired, be made large (for example, they can be wide straps or bands 21a, 22a) to prevent the head from moving back since it is generally not desirable to apply cervical traction when the head is moved back.

Figure 4:
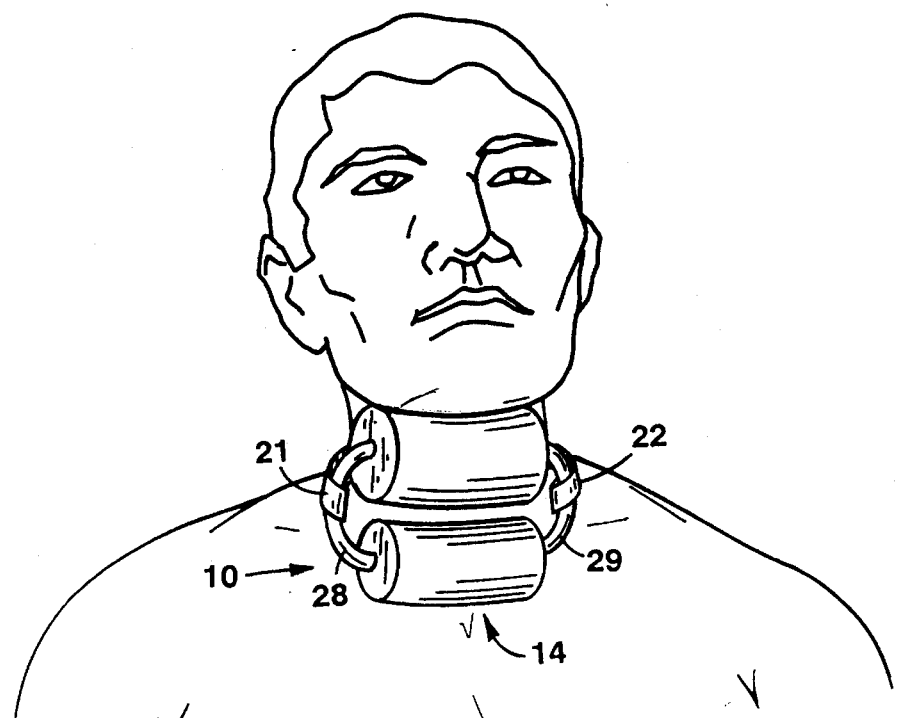
FIG. 4 is a diagrammatic representation of a front view of a person, showing the invention in use.

Referring now to FIG. 4, which is a front view of the device in operation, the device advantageously has rounded surfaces 28, 29 adjacent those sections in contact with the chest. These rounded surfaces provide a rolling action which enables the head to move and/or rotate laterally from side to side, as the portion 12 translates in response to lateral head movement.

It is also important to recognize that unlike a "collar" which has limited flexibility and adaptability, the device of the present invention enables the user not only to rotate the head laterally, but also to look down (for example to see where one is walking), to wear the device for a twenty-four hour period as is typically prescribed by the inventor, and to enable devices of different sizes and tensions to be easily manufactured for the wide variety of individuals who have need for the device.

Referring now to FIG. 2, there is illustrated another embodiment of the invention in which the tensioning materials do not extend beneath the cushioning material 18 but stop prior to entering that region. Accordingly, a more comfortable fit at the chin can be obtained by distributing the force beneath the chin over a larger area. In this manner, the total force can be increased, by increasing the stiffness of the spring materials 38, without increasing the discomfort of the wearer. The embodiment of FIG. 2 thus has the appearance and effect of a sling beneath the chin. In one particular embodiment, the material 40 which will be positioned beneath the chin is made more pliant and flexible to both increase the sling effect and render the device more comfortable.

It should be clear to one practiced in this field that many different combinations and shapes can be realized in manufacturing a device according to the invention. Thus, the structure can be a single molded material of plastic, rubber, or other man-made or natural materials, either in solid, honeycomb, hollow, or other form. The structure can further be constructed in various shapes, that is, it need not be round, oval, elliptical, or any other predefined shape except that it should provide the action necessary to enable the head to move back and forth, up and down, and side to side. In addition, the ring need not be a single continuous material but can be joined in sections, can have some straight sided sections so long as the above-identified criteria are met. The spring material can be, for example, fiberglass, teflon, etc. and can be embedded within a solid, honeycomb, hollow, inflatable, or other composition material, or the enclosing material itself can have the necessary spring characteristics. The cushioned materials 18 can be any desired foam or other cushioning materials to provide a comfortable and pliant surface, preferably one which adapts to the chin and chest surfaces with which it will be in contact.

The springs used to apply the force to create the traction necessary to treat the herniated cervical disc can include materials other than piano wire, including, for example, a coiled spring, and other elastic and springy materials which are well known to those in this field.

Additions, deletions, and other modifications of disclosed preferred embodiments of the invention will be apparent to those practiced in the art and are within the scope of the following claims.

What is claimed is:

1. An apparatus for applying traction to the cervical spine comprising a closed ring-shaped structure having first and second opposed portions at least one of which has a centrally located cushioned surface, said first and second opposed portions connected by a first and a second elastically deformable connecting member, said ring-shaped structure further comprising
an elongated hollow tubing, and
a spring material inserted within and extending longitudinally through the interior length of said hollow tubing, at least one of said first and second opposed portions, having a cushioned surface, being flexible and rounded for enabling a translational movement in response to lateral side to side movement of the head, a first and a second elongated tie-down connection member connected at one end to a respective one of the connecting members and arranged to securely connect to each other at their other ends, and whereby said ring-shaped structure can be placed between a person's chin and chest to provide an upward force against the underside of the chin, when said ring-shaped structure is held in operational position wherein said first and second elongated tie-down connection members are secured to each other behind the neck, said ring-shaped structure assumes a saddle shape and said first and second opposed portions provide a translational movement in response to lateral side to side movement of the head.

2. The traction apparatus of claim 1 wherein said spring material extends around substantially the entire circumference of said structure.

3. The traction apparatus of claim 1 wherein
said spring material extends around said circumference of said ring-shaped structure up to but not including the one of said first and second opposed portions to be placed under the chin.

4. An apparatus for applying traction to the cervical spine comprising a substantially closed ring-shaped structure having first and second opposed portions at least one of which has a centrally located cushioned surface, said first and second opposed portions connected by a first and a second elastically deformable connecting member, said ring-shaped structure being an elongated hollow tubing, at least one of said first and second opposed portions, having a cushioned surface, being flexible and rounded for enabling a translational movement in response to lateral side to side movement of the head, a spring material comprising piano wire inserted within and extending longitudinally through the interior length of said hollow tubing, a first and a second elongated tie-down connection member connected at one end to a respective one of the connecting members and arranged to securely connect to each other at their other ends, and whereby said ring-shaped structure can be placed between a person's chin and chest to provide an upward force against the underside of the chin, when said ring-shaped structure is held in operational position wherein said first and second elongated tie-down connection members are secured to each other behind the neck, said ring-shaped structure assumes a saddle shape and said first and second opposed portions provide translational movement of one portion in response to lateral side to side movement of the head.

5. The traction apparatus of claim 3 wherein said elongated hollow tubing comprises a first less pliant tubing for holding said spring material, and a second more pliant material for positioning beneath the chin during use.

6. The traction apparatus of claim 1 wherein said ring-shaped structure is closed and comprises an extruded elastic spring material.

7. The traction apparatus of claim 1 wherein said tie-down connection members each comprise a wide band member for resisting, when they are connected, a backward movement of the head.

8. The traction apparatus of claim 1 wherein said tie-down connection members comprise, at said other ends, loop and hook fasteners for connecting said other ends to each other.

9. The traction apparatus of claim 1 further wherein said ring-shaped structure comprises a molded pliant elastic material.

10. The traction apparatus of claim 1 further wherein said apparatus exerts, in operation, a force of at least five pounds against the underside of the chin.

11. A method for applying traction to the cervical spine comprising the steps of providing a ring-shaped spring elastic structure having an elongated hollow tubing and a spring material inserted within and extending longitudinally through the interior length of said hollow tubing, and at least one partially cushioned member, placing said ring-shaped structure with a said cushioned member beneath the chin and the opposing side of the structure from said cushioned member, against the chest, and bending said ring-shaped structure toward the throat to achieve a saddle shape and securing said structure behind the neck, enabling the spring of the bent ring-shaped structure to act upon and apply force beneath the chin, thereby to apply traction to a herniated cervical disc.

12. The traction applying method of claim 11 wherein said force is at least five pounds.

\* \* \* \* \*